United States Patent
Constantz et al.

(10) Patent No.: US 7,252,833 B2
(45) Date of Patent: *Aug. 7, 2007

(54) CALCIUM PHOSPHATE CEMENTS COMPRISING AN OSTEOCLASTOGENIC AGENT

(75) Inventors: Brent R. Constantz, Menlo Park, CA (US); David Delaney, Scotts Valley, CA (US)

(73) Assignee: Skeletal Kinetics, LLC, Cupertino, CA (US)

( * ) Notice: Subject to any disclaimer, the term of this patent is extended or adjusted under 35 U.S.C. 154(b) by 411 days.

This patent is subject to a terminal disclaimer.

(21) Appl. No.: 10/717,171

(22) Filed: Nov. 18, 2003

(65) Prior Publication Data
US 2005/0106260 A1    May 19, 2005

(51) Int. Cl.
*A61K 33/42* (2006.01)
*A61K 31/00* (2006.01)
*A61K 31/695* (2006.01)
*A61F 2/00* (2006.01)
*A01N 59/26* (2006.01)
*A01N 61/00* (2006.01)
*A01N 55/00* (2006.01)

(52) U.S. Cl. .................. 424/423; 424/70.12; 424/602; 514/1; 514/63

(58) Field of Classification Search ............. 424/70.12, 424/423, 602; 514/1, 63
See application file for complete search history.

(56) References Cited

U.S. PATENT DOCUMENTS

| | | |
|---|---|---|
| 4,160,012 A | 7/1979 | Ono et al. |
| 4,161,511 A | 7/1979 | Shiraki et al. |
| 4,429,691 A | 2/1984 | Niwa et al. |
| 4,497,075 A | 2/1985 | Niwa et al. |
| 4,990,163 A | 2/1991 | Ducheyne et al. |
| 5,281,265 A | 1/1994 | Liu |
| 5,525,148 A | 6/1996 | Chow et al. |
| 5,545,254 A | 8/1996 | Chow et al. |
| 5,580,623 A | 12/1996 | Fulmer et al. |
| 5,679,294 A | 10/1997 | Umezu et al. |
| 5,695,729 A | 12/1997 | Chow et al. |
| 5,697,981 A | 12/1997 | Ison et al. |
| 5,900,254 A | 5/1999 | Constantz |
| 5,954,867 A | 9/1999 | Chow et al. |
| 5,962,028 A | 10/1999 | Constantz |
| 5,968,253 A | 10/1999 | Poser et al. |
| 5,976,234 A | 11/1999 | Chow et al. |
| 5,997,624 A | 12/1999 | Chow et al. |
| 6,005,162 A | 12/1999 | Constantz |
| 6,017,729 A | 1/2000 | Anderson et al. |
| 6,027,742 A | 2/2000 | Lee et al. |
| 6,139,578 A | 10/2000 | Lee et al. |
| 6,375,935 B1 | 4/2002 | Constantz |
| 6,479,635 B1 | 11/2002 | Anderson et al. |
| 6,508,838 B2 | 1/2003 | Lee et al. |
| 6,528,482 B1 | 3/2003 | Anderson et al. |
| 6,537,763 B2 | 3/2003 | Dougall et al. |
| 2002/0155167 A1 | 10/2002 | Lee et al. |
| 2003/0050223 A1 | 3/2003 | Lam et al. |
| 2003/0199615 A1 | 10/2003 | Chaput et al. |
| 2004/0002770 A1* | 1/2004 | King et al. .............. 623/23.51 |
| 2004/0076686 A1 | 4/2004 | Tas |

OTHER PUBLICATIONS

Chow et al. Diametral tensile strength and compressive strength of a calcium phosphate cement: effect of applied pressure J. Biomed. Mater. Res. (Appl Biomat) 2000, 53, 511-517.*
Koide et al. Biochemical and Biophysical Research Communications 1999, 259, 97-102.*
Anderson et al. "A homologue of the TNF receptor and its ligand enhance T-cell growth and dendritic-cell function" *Nature* vol. 390, Nov. 13, 1997 pp. 175-179.
Lacey et al. "Osteoprotegerin Ligand in a Cytokine that Regulates Osteoclast Differentiation and Activation" *Cell* (1998) 93:165-176.
Wong et al. "TRANCE is a Novel Ligand of the Tumor Necrosis Factor Receptor Family That Activates c-Jun N-terminal Kinase in T Cells" *The Journal of Biological Chemistry* vol. 272, No. 40 10-3-1997, pp. 25190-25194.
Yasuda et al. "Osteoclast differentiation factor is a ligand for osteoprotegerin/osteoclastogenesi-inhibitory factr and is identical to TRANCW/RANKL" *Proc. Natl, Acad Sci. USA* vol. 95, pp. 3597-3602, Mar. 1998.

* cited by examiner

*Primary Examiner*—Johann Richter
*Assistant Examiner*—Ernst Arnold
(74) *Attorney, Agent, or Firm*—Bret E. Field; Bozicevic, Field & Francis LLP

(57) ABSTRACT

Methods and compositions are provided for producing flowable compositions, e.g. pastes, that set into calcium phosphate products that include an osteoclastogenic agent. In the subject methods, dry reactants that include a calcium source and a phosphate source are combined with a setting fluid and an osteoclastogenic agent, e.g., RANKL or a mimetic thereof, and the combined reactants are mixed to produce the flowable composition. Also provided are the compositions themselves as well as kits for preparing the same. The subject methods and compositions produced thereby find use in a variety of applications, including hard tissue repair applications.

21 Claims, No Drawings

CALCIUM PHOSPHATE CEMENTS COMPRISING AN OSTEOCLASTOGENIC AGENT

FIELD OF THE INVENTION

The field of this invention is calcium phosphate cements.

BACKGROUND

Calcium phosphate cements that are prepared by combining a dry component(s) and a liquid to form a flowable paste-like material that is subsequently capable of setting into a solid calcium phosphate product hold great promise for use as structural materials in the orthopedic and dental fields. For example, it is desirable to be able to inject a flowable material into a cancellous bone void and have the material set into a solid calcium phosphate mineral product that is capable of withstanding physiological loads. Materials that set into solid calcium phosphate mineral products are of particular interest as such products can closely resemble the mineral phase of natural bone and are susceptible to remodeling, making such products extremely attractive for use in orthopedics and related fields.

While a large number of different calcium phosphate cement formulations have been developed, there is a continued need for the development of yet more advanced formulations.

RELEVANT LITERATURE

United States patents of interest include: U.S. Pat. Nos. 6,375,935; 6,139,578; 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; 4,429,691; 4,161,511 and 4,160,012.

Also of interest are U.S. Pat. Nos. 6,537,763; 6,528,482; 6,479,635; and 6,017,729; U.S. Published Application No. 20030050223; and GENBANK accession no. NP_003692; as well as: Anderson et al., Nature (1997) 390:175-179; Lacey et al., Cell (1998) 93:165-176; Wong et al., J. Biol. Chem. (1997) 272: 190-194; and Yasuda et al., Proc. Nat'l Acad. Sci. USA (1998) 95: 3597-3602.

SUMMARY OF THE INVENTION

Methods and compositions are provided for producing flowable compositions, e.g. pastes, that set into calcium phosphate products that include an osteoclastogenic agent. In the subject methods, dry reactants that include a calcium source and a phosphate source are combined with a setting fluid and an osteoclastogenic agent, e.g., RANKL or a mimetic thereof, and the combined reactants are mixed to produce the flowable composition. Also provided are the compositions themselves as well as kits for preparing the same. The subject methods and compositions produced thereby find use in a variety of applications, including hard tissue repair applications.

DESCRIPTION OF THE SPECIFIC EMBODIMENTS

Methods and compositions are provided for producing flowable compositions, e.g., pastes, that set into calcium phosphate products that include an osteoclastogenic agent. In the subject methods, dry reactants that include a calcium source and a phosphate source are combined with a setting fluid and an osteoclastogenic agent, e.g., RANKL or a mimetic thereof, and the combined reactants are mixed to produce the flowable composition. Also provided are the compositions themselves as well as kits for preparing the same. The subject methods and compositions produced thereby find use in a variety of applications, including hard tissue repair applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

In further describing the subject invention, the subject methods will be described first, followed by a description of the compositions produced thereby, kits for use in preparing the same and methods for using the subject compositions in methods of hard tissue, e.g. bone repair.

METHODS

In the subject methods, dry reactants that include a calcium source and a phosphate source are combined with a setting fluid and an osteoclastogenic agent under conditions sufficient to produce a settable, e.g., flowable, composition that includes the osteoclastogenic agent and sets into a calcium-phosphate containing product, even when immersed in a fluid environment.

In the subject methods, the dry reactants include a calcium source and a phosphate source. The dry reactants are typically particulate compositions, e.g., powders, where the particle size of the components of the particulate compositions typically ranges from about 1 to about 1000 microns, usually from about 1 to about 200 microns and more usually from about 1 to about 40 microns.

As mentioned above, the dry reactants include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2 \cdot H_2O$); DCPD (dicalcium phosphate dihydrate, brushite or $CaHPO_4 \cdot 2H_2O$), ACP (amorphous calcium phosphate or $Ca_3(PO_4)_2H_2O$), DCP (or DCPA) (dicalcium phosphate, monetite or $CaHPO_4$), tricalcium phosphate (TCP), including both α- and β-$(Ca_3(PO_4)_2$, tetracalcium phosphate $(Ca_4(PO_4)_2O$, etc. Calcium sources of interest include, but are not limited to: calcium carbonate ($CaCO_3$), calcium oxide (CaO), calcium hydroxide ($Ca(OH)_2$) and the like. Phosphate sources of interest include, but are not limited to: Phosphoric acid ($H_3PO_4$), all soluble phosphates, and the like.

A variety of calcium phosphate cement compositions are known to those of skill in the art, and such cements may be readily modified into cements of the subject invention by including an osteoclastogenic agent, as described below. Cement compositions known to those of skill in the art and of interest include, but are not limited to, those described in U.S. Pat. Nos. 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

The ratios or relative amounts of each of the disparate calcium and/or phosphate compounds in the dry reactant mixture is one that provides for the desired calcium phosphate product upon combination with the setting fluid and subsequent setting. In many embodiments, the overall ratio (i.e., of all of the disparate calcium and/or phosphate compounds in the dry reactants) of calcium to phosphate in the dry reactants ranges from about 4:1 to 0.5:1, usually from about 2:1 to 1:1 and more usually from about 1.9:1 to 1.33:1.

The second component of the subject cement compositions is a setting fluid, as summarized above. The setting fluid can be any of a variety of setting fluids known to those of skill in the art. Setting fluids include a variety of physiologically compatible fluids, including, but are not limited to: water (including purified forms thereof), aqueous alkanol solutions, e.g. glycerol, where the alkanol is present in minor amounts, preferably less than about 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of about 0.01 to about 2M, such as from about 0.05 to about 0.5M, and at a pH in the range of about 6 to about 11, such as from about 7 to about 9, including from about 7 to about 7.5; and the like.

Of particular interest in certain embodiments is a silicate setting fluid, i.e., a setting fluid that is a solution of a soluble silicate. By solution of a soluble silicate is meant an aqueous solution in which a silicate compound is dissolved and/or suspended. The silicate compound may be any compound that is physiologically compatible and is soluble in water. By soluble in water is meant a concentration of at least about 1%, usually at least about 2% and more usually at least about 5%, where the concentration of the silicate employed typically ranges from about 0-0.1 to 20%, usually from about 0.01-5 to 15% and more usually from about 5 to 10%.

Representative silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tetramethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference. Of particular interest in many embodiments are solutions of sodium silicate, where the manufacture of dry sodium silicate ($Na_2SiO_3$, $Na_6Si_2O_7$ and $Na_2Si_3O_7$) is described in Faith, Keyes & Clark's INDUSTRIAL CHEMICALS (1975) pp 755-761.

Silicate setting fluids finding use with calcium phosphate cements are further described in U.S. Pat. No. 6,375,935; the disclosure of which is herein incorporated by reference.

In certain embodiments, the solution may further include an amount of phosphate ion, as described in U.S. application Ser. No. 10/462,075; the disclosure of which is herein incorporated by reference.

As summarized above, a feature of the subject cement compositions is that they further include an osteoclastogenic agent. By osteoclastogenic agent is meant an agent that induces osteoclastogenesis, i.e., causes differentiation of hematopoietic monocyte/macrophage precursors into osteoclasts. In many embodiments, the osteoclastogenic agent is a modulator of the RANK mediated osteoclastogenesis induction pathway. As such, the agent may modulate the activity of one or more members of the RANK mediated osteoclastogenesis induction pathway, e.g., TRAF6, NK-κB1, NF-κB2, c-fos, RANKL, etc. In many embodiments, the osteoclastogenic agent is typically an enhancer of the RANK mediated osteoclastogenic induction pathway. In many embodiments, the osteoclastogenic agent is a ligand for the RANK receptor. The RANK receptor is known and described in U.S. Pat. Nos. 6,537,763; 6,528,482; 6,479,635; and 6,017,729; the disclosures of which are herein incorporated by reference.

In those embodiments where the osteoclastogenic agent is a RANK ligand, the osteoclastogenic agent is typically an agonist of RANK, i.e., a RANK agonist. In certain embodiments, the RANK agonist is a RANKL polypeptide, by which is meant a polypeptide that binds to and activates the RANK receptor to induce osteoclastogenesis. The term polypeptide composition as used herein refers to both full-length proteins as well as portions or fragments thereof. Also included in this term are variations of the naturally occurring proteins, where such variations are homologous or substantially similar to the naturally occurring protein, as described in greater detail below, be the naturally occurring protein the human protein or a protein from some other species that naturally expresses RANKL, usually a mammalian species. In the following description of the subject invention, the name for a given repressor protein is used to refer not only to the human form of the protein, but also to homologs thereof expressed in non-human species, e.g., murine, rat, monkey and other mammalian species.

Of particular interest in certain embodiments is the RANKL (ligand to receptor activator of NFκB ligand) protein that has an amino acid sequence that includes a sequence that is substantially the same as, or identical to, the sequence of the human RANKL protein (also known as osteoprotegrin-ligand (OPG-L); TNF-related activation-induced cytokine (TRANCE), osteoclast different factor (ODF), and TNFS11), whose sequence is provided in GENBANK accession no. NP_003692 and described in: Anderson et al., Nature (1997) 390:175-179; Lacey et al., Cell (1998) 93:165-176; Wong et al., J. Biol. Chem. (1997) 272: 190-194; and Yasuda et al., Proc. Nat'l Acad. Sci. USA (1998) 95: 3597-3602.

By "substantially the same as" is meant a protein having a sequence that has at least about 50%, usually at least about 60% and more usually at least about 75%, and in many embodiments at least about 80%, usually at least about 90% and more usually at least about 95%, 96%, 97%, 98% or 99% sequence identity with the sequence of the above provided sequence, as measured by the BLAST compare two sequences program available on the NCBI website using default settings.

In addition to the specific RANKL proteins described above, homologs or proteins (or fragments thereof from other species, i.e., other animal species, are also provided, where such homologs or proteins may be from a variety of different types of species, usually mammals, e.g., rodents, such as mice, rats; domestic animals, e.g. horse, cow, dog, cat; and primates, e.g., monkeys, baboons, humans etc. By homolog is meant a protein having at least about 35%, usually at least about 40% and more usually at least about 60% amino acid sequence identity to the specific human transcription repressor factors as identified above, where sequence identity is determined using the algorithm described supra.

In addition to the naturally occurring RANKL proteins, polypeptides that vary from the naturally occurring proteins are also provided. By polypeptide is meant proteins having an amino acid sequence encoded by an open reading frame (ORF) of a repressor protein gene, described below, including the full length protein and fragments thereof, particularly biologically active fragments and/or fragments corresponding to functional domains, and including fusions of the subject polypeptides to other proteins or parts thereof, e.g., immunoglobulin domains. Fragments of interest will typically be at least about 10 aa in length, usually at least about 50 aa in length, and may be as long as 300 aa in length or longer, but will usually not exceed about 315 aa in length.

Also provided by the subject invention are non RANKL protein ligands having RANK binding activity. The term ligand, as used herein, refers to any compound capable of binding RANK and having an agonistic effect, and as such includes proteins and peptides, oligosaccharides, and the like, as well as binding mimetics thereof, including small molecule binding mimetics thereof. The subject ligands are capable of binding to RANK in a manner analogous to the binding activity of RANKL, and will generally comprise the functional RANK binding domain of a RANKL protein according to the subject invention, or the functional equivalent thereof.

For example, in certain embodiments the osteoclastogenic agent is a small molecule mimetic of RANKL. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

The osteoclastogenic agent as described above may be initially present as a component separate from the dry reactants and setting fluid components, or combined with one or both of these initially disparate components, such that it may be present in the dry reactants and/or setting fluid when the dry reactants and setting fluid are combined, as described below. One or both of the above liquid and dry reactant components may include an active agent that modulates the properties of the product into which the flowable composition prepared by the subject method sets. Such additional ingredients or agents include, but are not limited to: organic polymers, e.g., proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include, but are not limited to: osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g., NaCl, calcium sulfate; sugars, e.g., sucrose, fructose and glucose; pharmaceutically active agents, e.g., antibiotics; and the like.

In practicing the subject methods, suitable amounts of the dry reactants, the setting fluid and the osteoclastogenic agent are combined to produce a settable or flowable composition. In other words, the ratio of the dry reactants to setting fluid (i.e. the liquid to solids ratio) is selected to provide for a "settable" or "flowable" composition, where by "settable" or "flowable" composition is meant a composition that goes from a first non-solid (and also non-gaseous) state to a second, solid state after setting. In many embodiments, the liquid to solids ratio is chosen to provide for a flowable composition that has a viscosity ranging from that of milk to that of modeling clay. As such, the liquids to solids ratio employed in the subject methods typically ranges from about 0.2 to 1.0, usually from about 0.3 to 0.6. Of particular interest in many embodiments are methods that produce a paste composition, where the liquid to solids ratio employed in such methods typically ranges form about 0.25 to 0.5, usually from about 0.3 to 0.45.

The amount of osteoclastogenic agent that is combined with the dry and liquid components, described above, is sufficiently great to provide for the desired amount of osteoclastogenesis induction. The amount of osteoclastogenic that is present in the cement may vary, but in many certain representative embodiments ranges from about 1% to about 0.001% by weight, such as from about 0.5% to about 0.005% by weight, including from about 0.05% to about 0.01% by weight.

As mentioned above, the requisite amounts of dry reactants, setting fluid and osteoclastogenic agent (which may be separate from or present in one or both of the dry reactants and setting fluid) are combined under conditions sufficient to produce the flowable product composition. As such, the dry and liquid components are typically combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference. Also of interest is vibratory mixing, as described in U.S. patent application Ser. No. 10/661,356, the disclosure of which is herein incorporated by reference.

In certain embodiments, a simple cylindrical tube may be used both as a storage and packaging device and a mixing and delivery device. The plastic tube or analogous containment structure is separated into at least two sections, compartments or portions. One section or portion contains the powder component, as described above. The at least one more compartment contains the setting fluid, where in certain embodiments, two or more compartments for setting fluid components are provided, e.g., where it is desired to keep the disparate components of the setting fluid separate prior to use, and/or where one desires to have flexibility in determining the amounts of the phosphate and silicate ions in the setting fluid that is employed. For example, one may have a two-compartment device with powder in one component and a setting fluid in the other. In other embodiments, one may have a three compartment device, with powder in a first compartment, silicate solution in a second compartment and phosphate solution in a third compartment. In yet other embodiments, one may have a multi-compartment device, with powder in a first compartment, a solution at one concentration of either or both component ions in a second compartment, and a solution at a second concentration of either or both component ions in a third compartment, etc., where this type of embodiment allows one to "tailor" the setting fluid employed depending on the particular application in which the cement is to be used. In yet other embodiments, one may have a three-compartment device with powder in the middle component and setting solution in the two outer components, where each setting solution may be the same or different. Additional compartments may be present for additional components as desired, e.g., osteoclastogenic agent, cement modifiers, etc.

The two or more compartments are separated from each other by an easily removable barrier that can be readily removed during preparation of the packaged cement. Any convenient removable barrier may be present in the device, where a representative barrier means of interest is a dialysis bag clip or analogous means. Another representative barrier means of interest is a frangible barrier, as described in WO 98/28068 and 5,362,654; the disclosures of which are herein incorporated by reference. When one is ready to mix, the clip or other barrier means between the areas (liquid(s) and powder) is removed (e.g., unclipped), and the contents are simply kneaded together by hand or other technique. The above steps may be performed through a second outer covering for sterility—i.e., the above-described package elements may be present in a second outer covering for sterility. The outer covering may then be removed and the mixed contents from the tube may be delivered from one end of the storage/mixing tube using a peristaltic action.

The above-described packaging may be further modified to include one or more additional components that are employed during use/delivery of the product composition, such as removable delivery elements, elements for transferring the product cement into an attached delivery element, elements that assist in combining the components to produce the desired product composition, etc.

The temperature of the environment in which combination or mixing of the dry and liquid components takes place is sufficient to provide for a product that has desired setting and strength characteristics, and typically ranges from about 0 to 50° C., usually from about 20 to 30° C. Mixing takes place for a period of time sufficient for the flowable composition to be produced, and generally takes place for a period of time ranging from about 15 to 100 seconds, usually from about 15 to 50 seconds and more usually from about 15 to 30 second.

The above-described protocols result in a flowable composition that is capable of setting into a calcium phosphate mineral product, as described in greater detail below, where the flowable composition is characterized by including an amount of an osteoclastogenic agent, where the amount may vary but in representative embodiments ranges from about 1% to about 0.001% by weight, such as from about 0.5% to about 0.005% by weight, including from about 0.05% to about 0.01% by weight.

SETTABLE/FLOWABLE COMPOSITIONS

The flowable compositions produced by the above-described methods are compositions that set into a biologically compatible, and often resorbable and/or remodelable, product, where the product is characterized by including calcium phosphate molecules not present in the initial reactants, i.e., that are the product of a chemical reaction among the initial reactants.

The term flowable is meant to include paste-like compositions, as well as more liquid compositions. As such, the viscosity time of the subject flowable compositions, defined as time periods under which the mixed composition injects through a standard Luer-lok fitting after mixing, typically ranges up to about 10 minutes, usually up to about 7 minutes, such as up to about 4 minutes. Of particular interest in many embodiments are paste compositions that have an injectable viscosity that injects in a time period ranging up to about 5 minutes, such as up to about 4 minutes. Pastes that stay paste-like for longer period may be displaced by bleeding bone once implanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to produce it, but typically ranges from about 2:1 to 1.33:1, usually from about 1.8:1 to 1.5:1 and more usually from about 1:7:1 to 1.6:1. Of particular interest in many embodiments are apatitic products, which apatitic products have a calcium to phosphate ratio ranging from about 2.0:1 to 1.33:1, including both hydroxyapatite and calcium deficient analogs thereof, including carbonate substituted hydroxyapatite (i.e. dahllite), etc. The subject paste-like composition is, in many embodiments, one that is capable of setting into a hydroxyapatitic product, such as a carbonated hydroxyapatite, i.e. dahllite, having a carbonate substitution of from about 2 to about 10%, usually from about 2 to about 8% by weight of the final product.

The period of time required for the compositions to harden or "set" may vary. By set is meant: the Gilmore Needle Test (ASTM C266-89), modified with the cement submerged under 37° C. physiological saline. The set times of the subject cements may range from about 30 seconds to 30 minutes, and will usually range from about 2 to 15 minutes and more usually from about 4 to 12 minutes. In many embodiments, the flowable composition sets in a clinically relevant period of time. By clinically relevant period of time is meant that the paste-like composition sets in less than about 20 minutes, usually less than about 15 minutes and often in less than about 10 minutes, where the composition remains flowable for at least about 1 minute, usually at least about 2 minutes and, in many embodiments, for at least about 5 minutes following combination or mixture of the precursor liquid and dry cement components.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of at least about 20, usually at least about 40 and more usually at least about 50 MPa, as measured by the assay described in Morgan, E F et al., 1997, Mechanical Properties of Carbonated Apatite Bone Mineral Substitute: Strength, Fracture and Fatigue Behavior. J. Materials Science: Materials in Medicine. V. 8, pp 559-570., where the compressive strength of the final apatitic product may be as high as 60 MPa or higher. Inclusion of the silicate in the setting liquid allows lower liquid to solids ratios to be employed which results in significantly higher compressive strengths. Compressive strengths can be obtained that range as high 100 to 200 MPa. In certain embodiments, the resultant product has a tensile strength of at least about 0.5 MPa, such as at least about 1 MPa, including at least about 5 MPa, at least about 10 MPa or more, e.g., from about 0.5 to about 10 MPa, as determined by the tensile strength assay appearing in the Experimental Section, below.

In many embodiments, the resultant product is stable in vivo for extended periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for at least about 4 months, at least about 6 months, at least about 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for at least about 4 months, at least about 6 months, at least about 1 year or longer, e.g., 2.5 years, 5 years, etc.

In many embodiments, the flowable paste-like composition is capable of setting in a fluid environment, such as an in vivo environment at a bone repair site. As such, the flowable paste composition can set in a wet environment, e.g., one that is filled with blood and other physiological fluids. Therefore, the site to which the flowable composition is administered during use need not be maintained in a dry state.

In certain embodiments, the subject cement compositions may be seeded with any of a variety of cells, as described in published U.S. patent application No. 20020098245, the disclosure of which is herein incorporated by reference.

In addition, in certain embodiments the compositions include demineralized bone matrix, which may be obtained typically in a lyophilized or gel form and is combined with the cement composition at some prior to implantation. A variety of demineralized bone matrixes are known to those of skill in the art and any convenient/suitable matrix composition may be employed. Alternatively, one or more polymeric agents may be added to the cement, as desired, e.g., collagen, or analogous agents known to be employed in cements.

In certain embodiments, the cements may include one or more collections of contrast particles (for example, for use as tracers during use of the cement), e.g., as described in U.S. Pat. No. 6,273,916; the disclosure of which is herein incorporated by reference.

Applications

The subject methods and compositions produced thereby, as described above, find use in applications where it is desired to introduce a flowable material capable of setting up into a solid calcium phosphate product into a physiological site of interest, such as in dental, craniomaxillofacial and orthopedic applications. In orthopedic applications, the cement will generally be prepared, as described above, and introduced to a bone repair site, such as a bone site comprising cancellous and/or cortical bone.

Representative orthopedic applications in which the cements prepared by the subject system find particular use include the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific dental, craniomaxillofacial and orthopedic indications in which the subject invention finds use include, but are not limited to, those described in U.S. Pat. No. 6,149,655, the disclosure of which is herein incorporated by reference. In addition to these particular applications described in this U.S. patent, the subject cement compositions also find use in applications where a sternotomy has been performed. Specifically, the subject cements find use in the closure process of a sternotomy, where the bone fragments are rejoined and wired together, and any remaining cracks are filled with the subject cement. In yet other embodiments, the subject compositions find use in drug delivery, where they are capable of acting as long lasting drug depots following administration to a physiological site. See e.g. U.S. Pat. Nos. 5,904,718 and 5,968,253; the disclosures of which are herein incorporated by reference.

KITS

Also provided are kits comprising the subject cements, where the dry and liquid components may be present in separate containers in the kit, or some of the components may be combined into one container, such as a kit wherein the dry components are present in a first container and the liquid components are present in a second container, where the containers may or may not be present in a combined configuration, as described in U.S. Pat. No. 6,149,655, the disclosure of which is herein incorporated by reference. In certain embodiments, the kits may include two or more setting fluids in different concentrations, e.g., where one wishes to provide a kit with flexibility with respect to the nature of the setting fluid that is prepared therefrom. For example, a kit may include two more different phosphate-silicate solutions that differ from each other with respect to their silicate and/or phosphate components. Alternatively, the kit may include to or more different, separate phosphate and/or silicate solutions that differ from each other in terms of concentration and that are mixed upon use of the kit as desired to obtain a desired setting fluid. As mentioned above, the kit components may be present in separate containers. Alternatively, the components may be present as a packaged element, such as those described above.

In addition to the cement compositions, the subject kits may further include a number of additional reagents, e.g., cells (as described above, where the composition is to be seeded), protein reagents (as described above), and the like.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Representative Formulation:

Powder:
6.0 grams TCP
0.6 Grams DCPA
0.2 Grams $NaH_2PO_4 \cdot H_2O$

Liquid:
$NaSiO_4$ 1/40 dilution, pH 11.10

To the above cement formulation, RANKL is added. RANKL may be added to the liquid setting solution. Alternatively, RANKL may be added to the cement as a separate solution, which may or may not include additionl cement modification agents, e.g., polymeric agents, such as collagen.

It is evident from the above results and discussion that calcium phosphate cements that include osteoclastogenic agents are provided. Benefits of the subject cements include improved remodelability as compared to cements that lack osteoclastogenic agents, e.g., in the form of faster replacement with natural bone. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of producing a flowable composition that sets into a calcium phosphate containing product, said method comprising combining:
   (a) a water soluble silicate setting fluid;
   (b) dry reactants comprising a calcium source and a phosphate source; and
   (c) an osteoclastogenic agent which is a RANK ligand, in a ratio of (a) to (b) sufficient to produce said flowable composition that goes from a non-solid state to solid calcium phosphate containing product after setting.

2. The method according to claim 1, wherein said setting fluid comprises said osteoclastogen ic agent.

3. The method according to claim 1, wherein said dry reactants comprise said osteoclastogenic agent.

4. The method according to claim 1, wherein said ligand for RANK is a RANKL polypeptide.

5. The method according to claim 4, wherein said RANKL polypeptide is a human RANKL.

6. The method according to claim 1, wherein said ratio ranges from about 0.2:1 to 0.7:1.

7. The method according to claim 6, wherein said flowable composition is a paste.

8. The method according to claim 1, wherein said flowable composition sets into said calcium phosphate containing product in a period of time ranging from about 5 to 10 minutes.

9. The method according to claim 1, wherein said calcium phosphate containing product has a compressive strength ranging from about 25 to 100 MPa.

10. A method of producing a paste that sets into a calcium phosphate containing product, said method comprising
   (a) combining:
      (i) a water soluble silicate setting fluid;
      (ii) dry reactants comprising a calcium source and a phosphate source; and
      (iii) an osteoclastogenic agent which is a RANK ligand, wherein said dry reactants, setting fluid and osteoclastogenic agent are combined in a ratio of said dry reactants to said setting fluid sufficient to provide for said paste; and
   (b) mixing said combined reactants and setting fluid for a sufficient period of time to produce a paste capable of setting into a calcium phosphate containing product.

11. The method according to claim 10, wherein said setting fluid comprises said osteoclastogen ic agent.

12. The method according to claim 10, wherein said dry reactants comprise said osteoclastogenic agent.

13. The method according to claim 10, wherein said ligand is a RANKL polypeptide.

14. The method according to claim 10, wherein said flowable composition sets into said calcium phosphate containing product in a period of time ranging from about 5 to 10 minutes.

15. The method according to claim 10, wherein said calcium phosphate containing product has a compressive strength ranging from about 25 to 100 MPa.

16. A flowable composition that sets into a solid calcium phosphate containing product, wherein said composition is produced by the method of claim 1.

17. A method of repairing a hard tissue defect, said method comprising:

applying to the site of said defect a flowable composition according to claim 16.

18. A kit for use in preparing a flowable composition that sets in an in vivo fluid environment into a solid calcium phosphate product said kit comprising:

(a) a water soluble silicate setting fluid;
(b) dry reactants comprising a calcium source and a phosphate source; and
(c) an osteoclastogenic agent which is a RANK ligand.

19. A packaged calcium phosphate cement, said packaged cement comprising: a tubular element separated into a first compartment and at least one additional compartment by a removable barrier; wherein (i) dry reactants comprising a source of calcium and phosphate present in said first compartment;
(ii) a water soluble silicate setting fluid or components thereof present in said at least one additional compartment; and
(iii) an osteoclastogenic agent which is a RANK ligand present in either said first compartment, said at least one additional compartment or in a second additional compartment.

20. The packaged calcium phosphate cement according to claim 19, wherein said removable barrier is a clip.

21. The packaged calcium phosphate cement according to claim 19, wherein said removable barrier is a frangible barrier.

* * * * *